United States Patent [19]

Revesz

[11] Patent Number: 5,620,659
[45] Date of Patent: *Apr. 15, 1997

[54] APPARATUS FOR PREVENTING EXPLOSIONS DURING MICROWAVE HEATED SOLVENT EXTRACTIONS

[75] Inventor: Robert N. Revesz, Monroe, N.C.

[73] Assignee: CEM Corporation, Matthews, N.C.

[ * ] Notice: The portion of the term of this patent subsequent to Jun. 9, 2013, has been disclaimed.

[21] Appl. No.: 515,357

[22] Filed: Aug. 15, 1995

Related U.S. Application Data

[63] Continuation-in-part of Ser. No. 74,324, Jun. 9, 1993, Pat. No. 5,443,795.
[51] Int. Cl.⁶ .............................. G05D 16/08; H05B 6/80
[52] U.S. Cl. .................. 422/90; 422/107; 422/109; 422/113; 422/117; 422/288; 219/679; 219/716
[58] Field of Search ................................... 422/78, 80, 90, 422/102, 103, 105, 107, 108, 109, 113, 117, 261, 288; 219/679, 686, 687, 707, 716

[56] References Cited

U.S. PATENT DOCUMENTS 4,311,895 1/1982 Tanabe .
4,347,216 8/1982 Kawasaki et al. .
4,637,145 1/1987 Sugisawa et al. .
4,877,624 10/1989 Floyd et al. .
5,230,865 7/1993 Hargett et al. .

*Primary Examiner*—Jeffrey Snay
*Attorney, Agent, or Firm*—Bell, Seltzer, Park & Gibson, P.A.

[57] ABSTRACT

A process for extracting extractable material from a base material in which it is present, while protecting against explosion of any solvent vapor in air includes heating by microwave radiation in a closed pressure-resistant and heat-resistant container, such base material, extractable material and organic extraction solvent, passing air near or into contact with the extraction container so that it will carry away from the container any escaping solvent vapor, and passing said air with the solvent vapor, if present, into contact with solvent detector which turns off a source of microwave radiation when the solvent vapor is present. Preferably the invented process will include passing the air, with any solvent vapor which may be present in it, to a flow detector, which will turn off the source of microwave radiation if flow ceases. The described processes may also include providing a rupture diaphragm to release extraction container contents at a pressure lower than that at which the container will fail, venting any contents exiting the container on to a collection container and venting vapor contents thereof to a solvent vapor detector. Also described are apparatuses for practicing the mentioned processes.

17 Claims, 6 Drawing Sheets

5,620,659

APPARATUS FOR PREVENTING EXPLOSIONS DURING MICROWAVE HEATED SOLVENT EXTRACTIONS

This application is a continuation-in-part of Ser. No. 08/074,324, filed Jun. 9, 1993, now U.S. Pat. No. 5,443,795.

This invention relates to solvent extraction processes. More particularly, it relates to such processes in which the solvent employed is explosive in air and is heated during the extraction by microwave radiation, which can result in dangerous explosive conditions if any of the solvent escapes from an extraction vessel and mixes with air in a microwave chamber, into which microwave radiation is being directed. Such conditions may be prevented by detecting the presence of solvent vapors at less than explosive conditions in exhaust air from the microwave chamber and turning off the source of microwave radiation in response to such detection. An additional protective feature of the invention is detecting any cessation of exhaust air flow past the solvent vapor detector, which could prevent operation of the solvent vapor detector, and turning off the source of microwave radiation if such air flow ceases. Also within the invention are apparatuses for accomplishing the described processes.

Digestions of materials in digesting liquids, such as strong acids, have been conducted in digesting systems wherein the digesting liquid was heated by microwave radiation. See, for example, European patent 0,416,759, European published specification 0,455,513 and U.S. Pat. No. 5,215,715. Extractions with solvents, wherein the solvent is sufficiently polar to absorb microwave radiation and convert it to heat, have been employed, too, as reported in Volume 371 of the Journal of Chromatography, at pages 299–306. A mixture of polar and non-polar solvents can be utilized, with the polar solvent absorbing microwave radiation and causing heating of the mixture. Although digesting acids are corrosive they are not usually explosive but many organic solvents are explosive when their vapors are mixed with air, so a safety problem can be encountered when conducting microwave heated extractions unless such problem is recognized and procedures are followed to prevent any such explosion.

The present invention prevents explosive incidents mentioned above by detecting the presence of very small quantities of solvent vapors in the exhaust air from a microwave chamber and shutting down the source of microwave radiation (which otherwise could cause ignition of an explosive mixture of solvent vapor and air in the microwave chamber if the solvent vapor concentration increased to explosive proportion) or shutting down the entire electrical system of the digesting apparatus in response to such detection. To be safe such shutdowns occur when the content of solvent vapor in air is less than the lowest explosive limit (LEL). Thus, the invention facilitates the early detection of any leak in the system or of any rupture of a safety diaphragm on the extracting vessel, the purpose of which diaphragm is to prevent explosive failure of the extracting vessel due to excess pressure that might be developed in it when the extracting solvent is heated excessively. European patent specification 0,455,513, the disclosure of which is hereby incorporated herein by reference, discloses such a rupture diaphragm in a digesting system and the details of construction and location can be the same for the present extraction systems. Similarly, European patent 0,416,759 teaches the presence of a collecting container for collecting any vented vapor and liquid from a digesting container that has blown its rupture diaphragm, and such structure, which is also present in a preferred extraction apparatus of the present invention, is also incorporated herein by reference. Additionally, the following references, cited by the Examiner in the prosecution of parent application Ser. No. 08/074,324, now U.S. Pat. No. 5,443,795, are of relevance: U.S. Pat. Nos. 3,185,109; 3,909,598; 4,162,381; 4,311,895; 4,331,855; 4,347,216; 4,484,065; 4,507,529; 4,637,145; 4,877,624; 5,206,479 and 5,230,865; Figaro Gas Sensor TGS 822 (January, 1989 [8 pages]); Figaro Products Information TGS-822 (August, 1992, [2 pages]); and Figaro Products Catalog (September, 1992, 12 pages]).

In accordance with the present invention a process for extracting an extractable material from a base material in which it is present, while protecting against explosion of any solvent vapor in air comprises microwave heating a solvent, which is explosive in air, in which solvent there is present a base material containing an extractable material, which heating is under pressure in an extraction vessel in an extraction system, passing air near said system so that it will carry away from said system any solvent vapor that escapes from said vessel, and passing said air, which contains solvent vapor when said vapor has escaped from said vessel, into contact with means for detecting said solvent vapor, which means modifies an electrical signal when said solvent vapor is present in said air, which modified electrical signal automatically turns off a source of microwave radiation that heats said solvent, extractable material and base material in the vessel. The invention also relates to an apparatus for practicing the described process and to an apparatus which also includes a flow rate detector or sensor which turns off a source of microwave radiation when gas flow ceases or becomes minimal. Such detector can be independent of the solvent detector or the solvent detector can possess flow detection properties. In some aspects of the invention all the sources of electricity relating to the process and apparatus are cut off when solvent vapor or lack of flow is detected, thereby ensuring that no spark can set off an explosion.

To supplement the safety features of the invention it is preferred to have the ceiling portion of the microwave chamber covered with an insulating polymeric plastic material, such as a fluoropolymer, e.g., polytetrafluoroethylene or PFA, and to have it cover a ceiling light, whereby sparking in the chamber at such locations is prevented and heat from the light is decreased, which help to prevent creations of potentially explosive conditions in the chamber.

A search of prior art references, conducted mainly in subclasses 219-10.55B and 219-10.55C, resulted in the finding of several patents that relate to microwave cooking, wherein the cooking process is controlled in response to gas sensors in the exhaust from the cooking chamber. Such patents include U.S. Pat. Nos. 3,185,809, 4,162,381, 4,311,895, 4,331,855, 4,484,065 and 4,507,529. The most relevant of these is considered to be the last listed, which shows the use of a Figaro Inc. sensor in the exhaust from a microwave cooking oven which detects various gaseous cooking byproducts. However, none of the patents found discloses use of such a detector to prevent creation of explosive conditions during microwave heated solvent extractions and none shows drawing off a gas from a collection container for released solvent from an extraction container, detecting solvent in the gas and shutting down the microwave source when it is detected.

The invention will be readily understood by reference to this specification, including the following detailed description, taken in conjunction with the appended drawing, in which.

Figure 1:
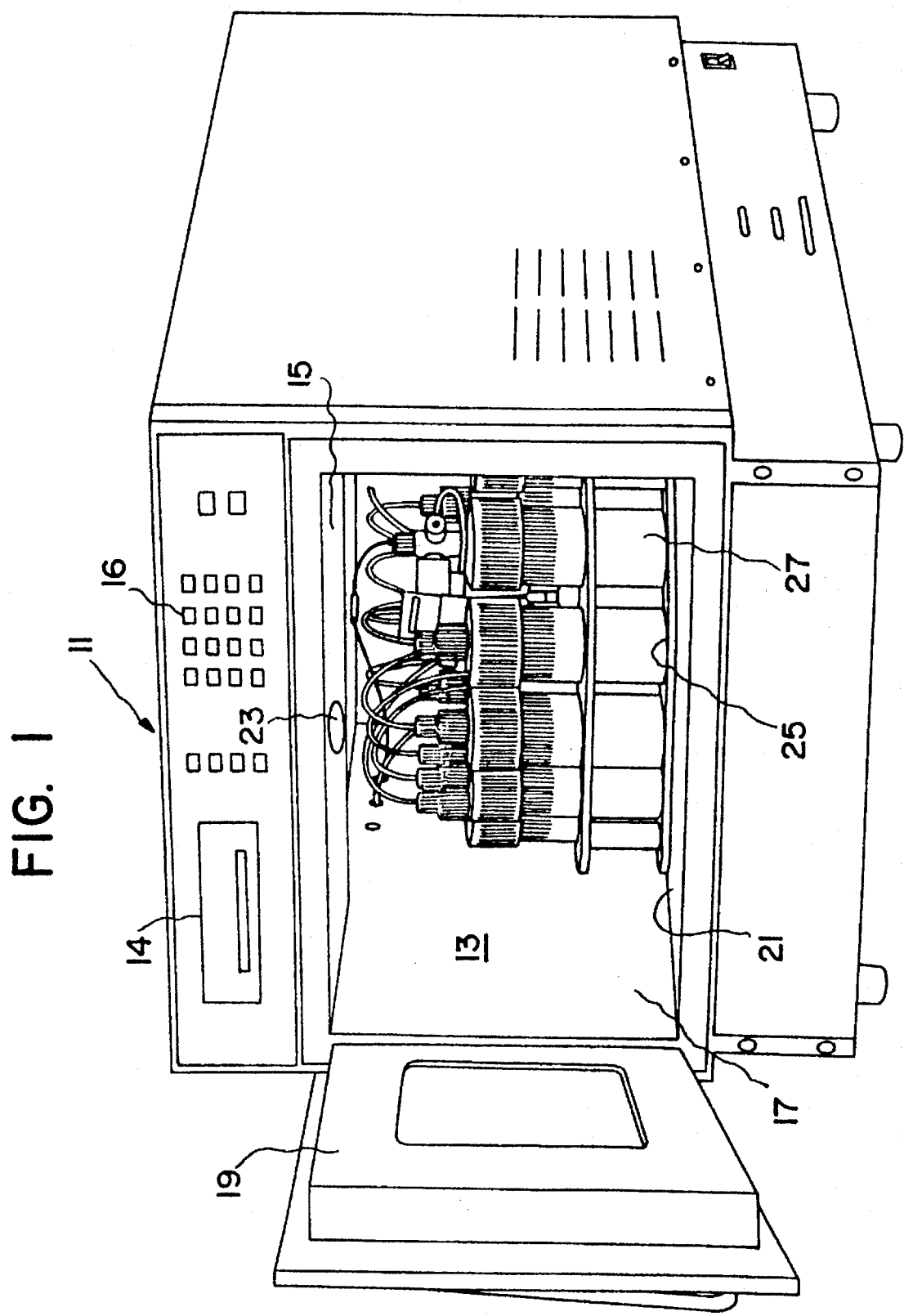
FIG. 1 is a front perspective view of a microwave heated solvent extraction apparatus of this invention.

In FIG. 1 microwave extraction apparatus or system 11 comprises a chamber 13 which includes a ceiling 15, three side walls 17, a door 19 and a floor 21, with the ceiling having mounted therein a light or lamp 23. A source of microwave radiation, such as a magnetron, not illustrated, directs microwave radiation into the chamber. In the chamber is mounted a turntable 25 on which are positioned a plurality of extraction containers 27. Further details of the extraction containers, their connections to a collection container and its connection to a solvent vapor detector will be given in the descriptions of FIGS. 2–5.

Figure 2:
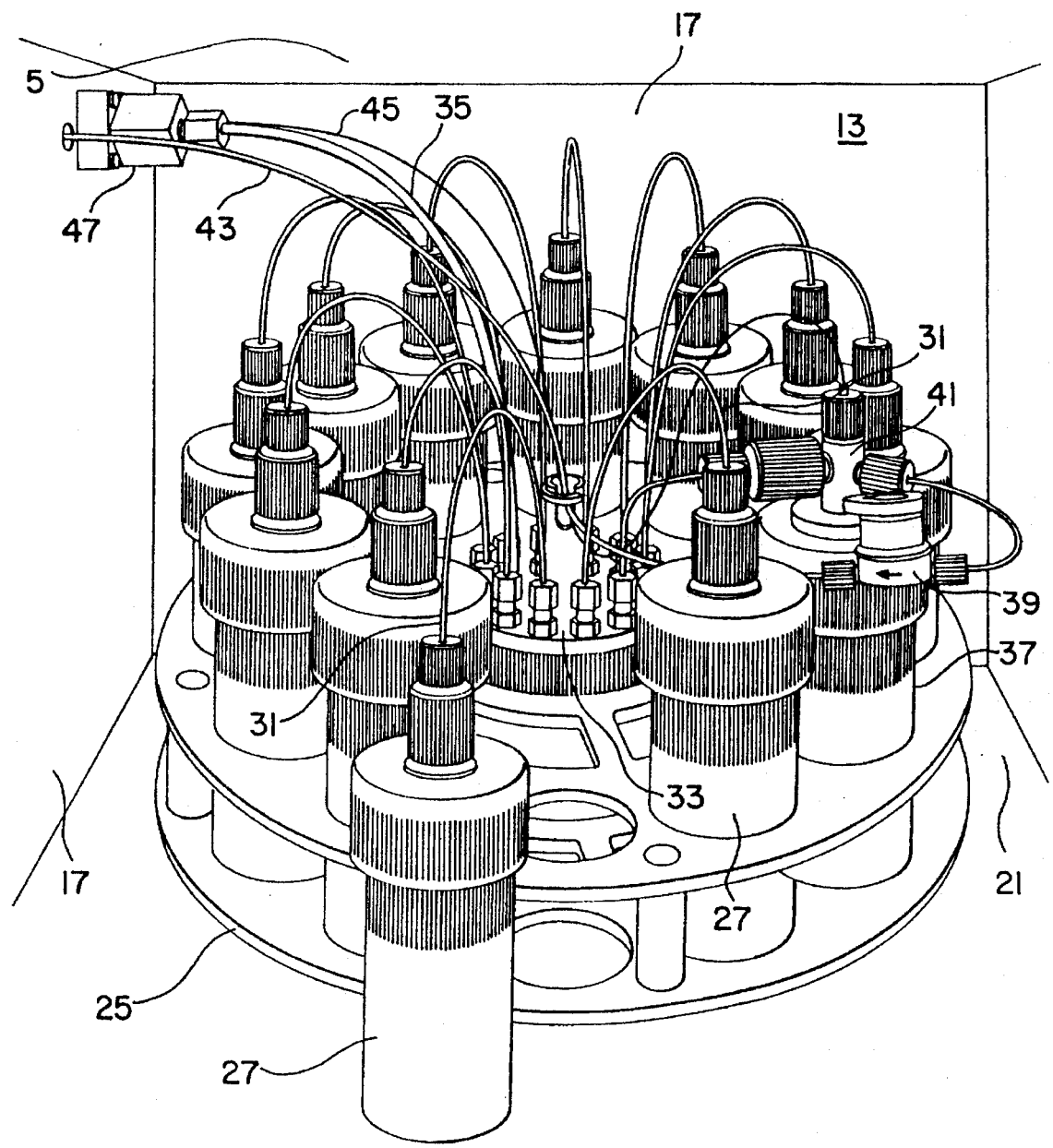
FIG. 2 is atop front perspective view of the microwave chamber of the invented apparatus, showing connections of the extraction containers to the collection container and of the collection container to a tube which leads to an area near the detector.

FIG. 2 illustrates in an enlarged view the positionings of the plurality of extraction vessels on the turntable in the microwave chamber, their connections to the collection container wherein any discharges from the extraction vessels, including solvent vapor and entrained liquid, are collected, and connection of the collection container head space (and solvent vapor therein) to solvent detecting and magnetron controlling means external of the microwave chamber. Extraction containers 27, all of which include rupture diaphragms 59 (see FIG. 3), each connect to tubes 31, which carry discharged vapor and any entrained material from containers whose rupture diaphragms have burst, due to the containers having reached their pre-set maximum design pressure, to collection container 33. The head space in container 33 is connected by another tube 35 to an exhaust duct that contains a vapor detector (both being illustrated in FIGS. 4 and 5). Mounting means for the tube 35 are shown at 47 and are adapted to mount tube 35 on chamber wall 17 and to fit it to an external tube, as in FIG. 4 (where it is mounted differently) that connects to a duct containing the solvent vapor detector. One of the extraction containers, designated 37, includes pressure probe means 39 and temperature probe means 41, connected by tubing 43 and fiber optics 45, respectively, to readout means, not shown specifically, but preferably in the area designated 14 in FIG. 1. Such probes allow an operator of the extraction apparatus to follow pressure and temperature changes in the extraction containers (assuming that such conditions are about the same in the various containers), and to control them, if desired.

Figure 3:
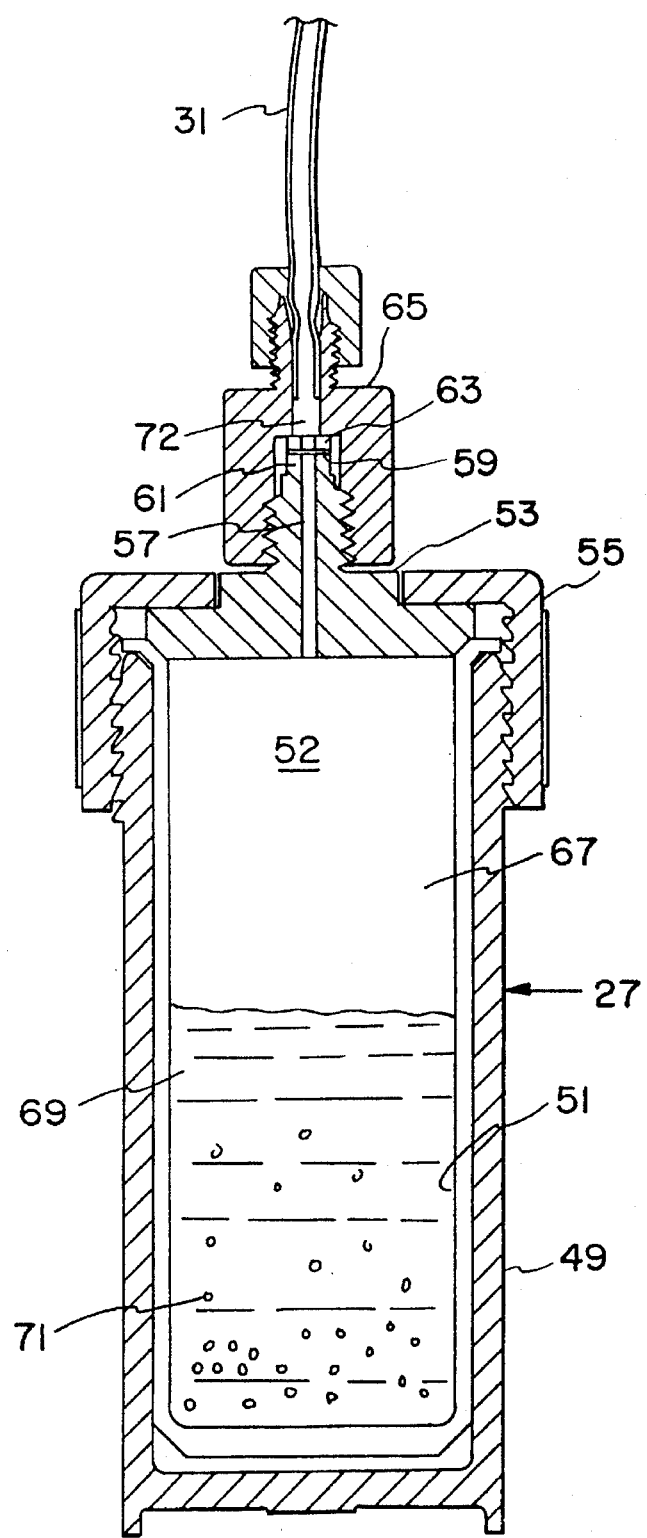
FIG. 3 is a central vertical sectional elevation of an extraction container utilized in the invention.

In FIG. 3 details of the construction of the extraction container are given. Such container may be the same as the digestion container described in European patent 0,416,759, had been previously referred to herein, or may be any suitable container that is microwave transmissive, heat stable and solvent resistant. Container 27 includes a body portion 49 which is pressure resistant (polyetherimide, such as ULTEM®, is a preferred material of construction and may be reinforced by continuous glass fibers or fabric) and a liner portion 51 which is solvent resistant (such as a fluoropolymer, e.g., TEFLON®), both such types of polymers being microwave radiation transmissive. A cover 53 of solvent resistant material (fluoropolymer is preferred) is held tightly by cap 55 to the liner 51 to seal off the extraction vessel extracting volume 52. Internal passageway 57 in cover 53 is normally blocked off by rupture diaphragm or membrane 59 which is held tightly to the passageway wall 61 by backup ring 63 and screw cap 65. However, if the design pressure for the rupture diaphragm is exceeded (and such design pressure may often be in the range of 50 to 1,000 lbs./sq. in., or 100 or 200 lbs./sq. in.) the contents of container 27, including solvent vapor 67, with any entrained liquid solvent 69 and material being extracted 71, will be vented through passage 72 and vent tube 31 to collection container 33 (shown in FIG. 2).

Figure 4:
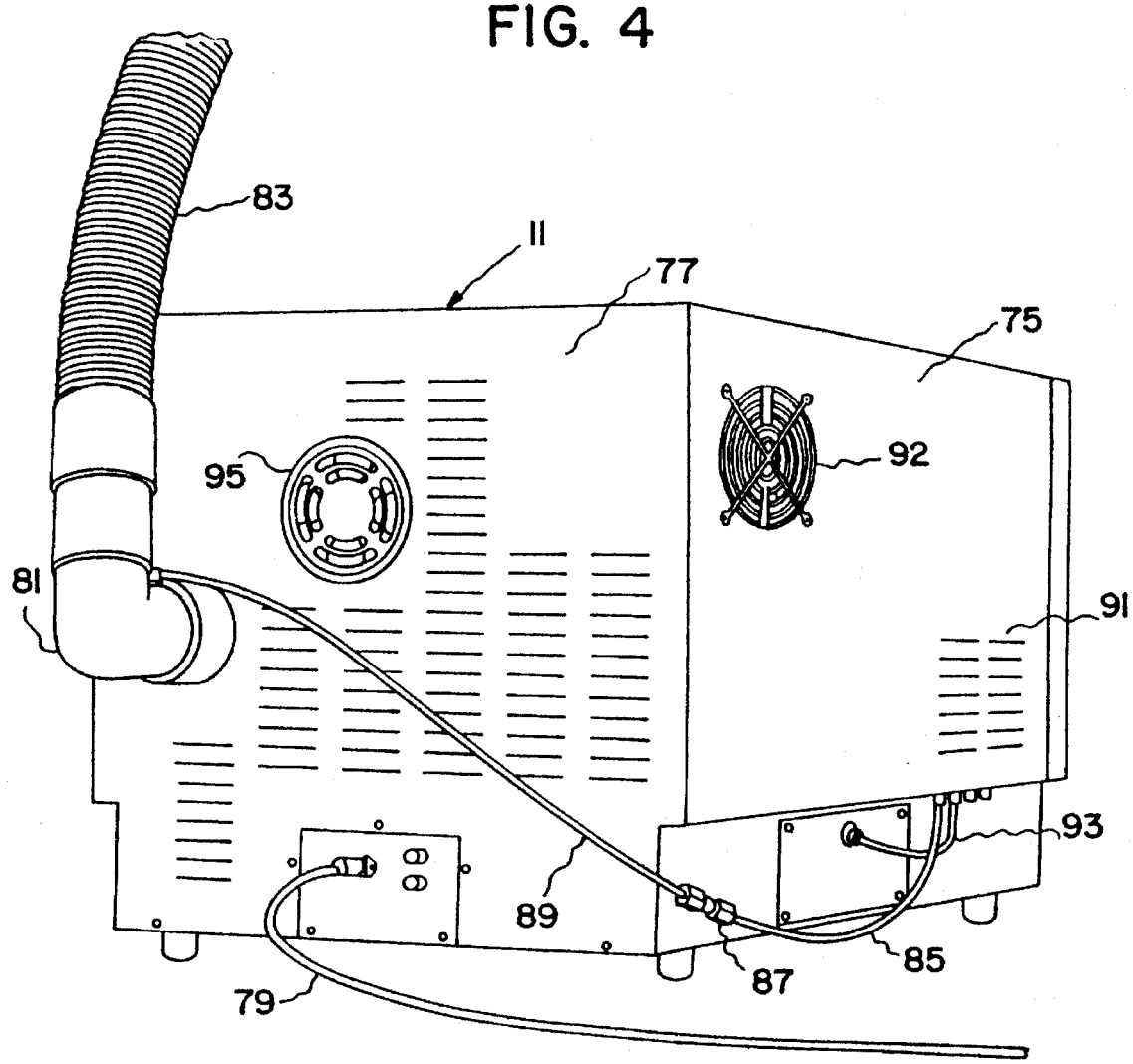
FIG. 4 is a rear perspective view of the apparatus.
Figure 5:
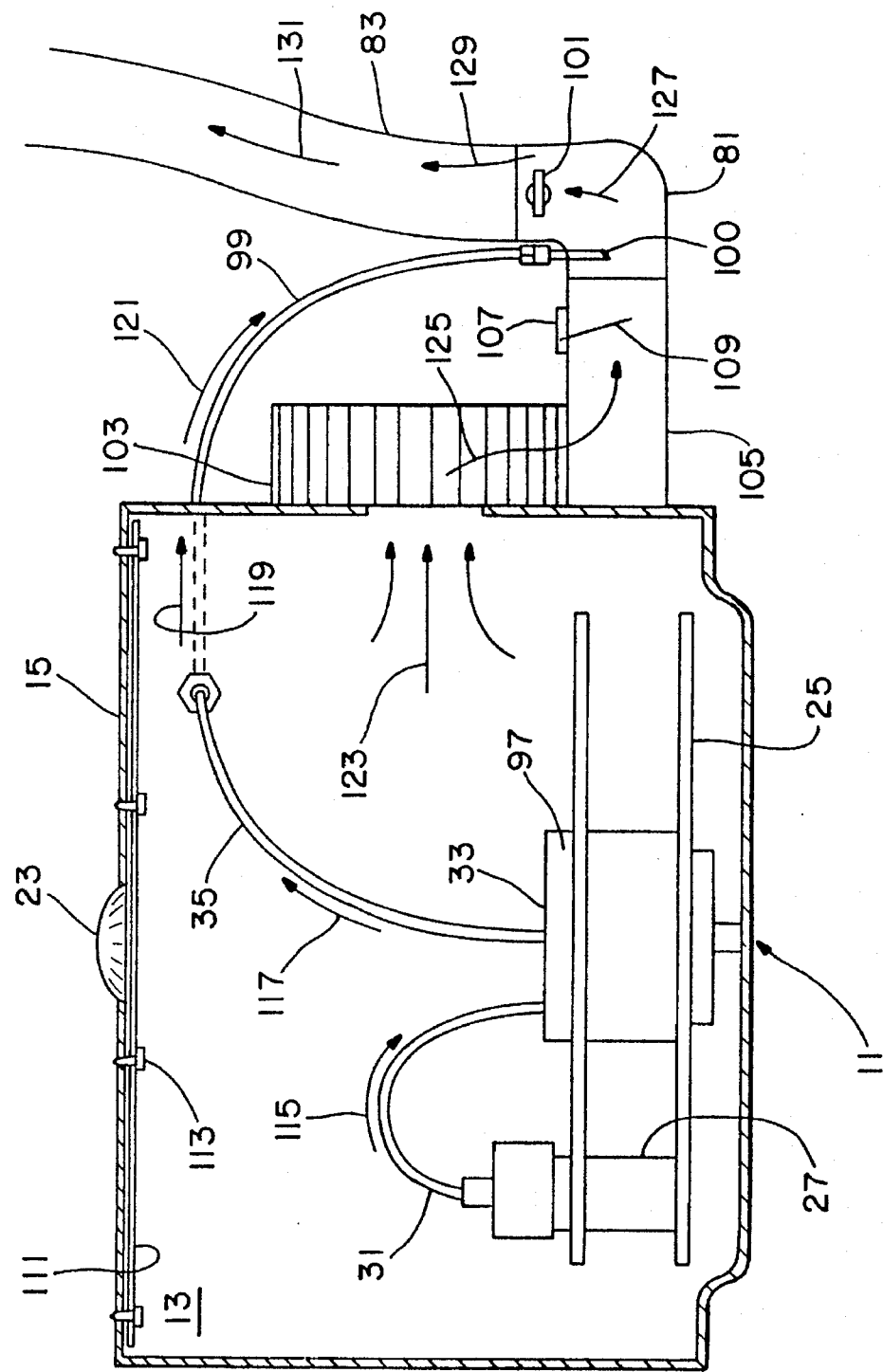
FIG. 5 is a schematic breakaway elevational view of the invented apparatus, showing relationships between an exhaust fan, a detector, the solvent vapor inlet, and an air flow detector/switch.

In FIG. 4 is shown the exterior side 75 and back 77 of microwave extraction system 11. Line 79 carries nominal 110 to 240 volt AC power to the electrical circuitry, which will be shown in detail in FIG. 6. A fan or blower motor back 95, with the blower shown somewhat differently in FIG. 5, as 103, acts to remove air and any contained solvent vapor from the microwave chamber and as in FIG. 5, when connected appropriately, passes such through elbow fitting 81 and duct 83 to outside the building in which the apparatus is located or to recovery and/or treatment means. Any solvent vapor that was vented to the collection container from an extraction vessel passes through tubing 85, coupling 87 and tubing 89 to elbow 81, in which it is discharged from a tube end that is angled to develop a reduced pressure that causes flow of the solvent vapor from the collection container to the elbow and thence out duct 83. Details of the tubing and connections are shown in FIG. 5. Pressure tubing 93, which communicates with the visual display 14, indicates the pressure in the probed container and may be utilized with a controller to control magnetron operation, as desired, to maintain a desired pressure and temperature in containers 27. Numeral 91 designates air inlet louvers to the microwave chamber. Similar louvers are located on the opposite side of the apparatus. Numeral 92 designates a cooling fan for the magnetron.

In FIG. 5 microwave solvent extraction chamber 13 contains an extraction vessel 27, from which a venting tube 31 communicates with closed collection container 33. Head space 97 of such collection container communicates via tubing 35 and tube 99 with the air stream in fitting 81, with tube 99 or an extension of it terminating at 100 in an angled opening in the air stream, with such opening facing downstream and being located near (usually within 15 cm) of the detector 101, which is positioned downstream of tube outlet 100. Fan or blower 103 draws air through microwave chamber 13 through inlet louvers 91 (FIG. 4) and blows it out through duct 105, elbow 81 and flexible ductwork 83 to the external atmosphere or a recovery or treatment facility. Because of the reduced pressure at the termination of tube 99 in elbow 81 at 100 and also sometimes because of the increased pressure in the collection container 33 solvent vapor from an extraction vessel whose rupture diaphragm has burst, sending the vapor to the collection container, is drawn through tubing 99 to the area of the detector 101. The detector thereby becomes of lower electrical resistance and an increased voltage results which actuates a relay or other switching device or circuitry (see FIG. 6) to shut down the magnetron or other microwave generator or, in some cases, the entire electrical system of the apparatus. Although positioning of the opening 100 upstream of detector 101 is preferred it has also been found that even when such positioning is reversed (with the opening angle facing downstream, the detector is activated by solvent vapor drawn from the collection container, possibly because a vapor surge drives the vapor against the air flow. Also, because of the sensitivity oft he detector it can detect even slight leakages in the rupture diaphragm seal, which leakages sometimes occur; it is not limited to detecting only pressure ruptures of the diaphragms. When a detector of the semiconductor gas sensor type, preferably a tin dioxide semiconductor type, is employed, such as a Figaro Engineering Inc. TGS822, which is of a high sensitivity to organic solvent vapors, reliable over a long period of use and capable of generating a large output signal for a simple, low cost circuit, the detector is also sensitive to air flow, with halted or lessened flow making it more highly conductive, so that when the chamber exhaust fan is not in operation or is slowed down appreciably, the magnetron or the entire system can be turned off by the detector. This is another safety feature of this invention because if the fan is not operating and solvent vapor is leaking into the microwave chamber explosive conditions could result unless the magnetron is turned off. Although the detector described will turn off the magnetron or other source of microwave radiation (or the entire system) when it detects solvent vapor or when the air flow is halted it is often preferred to include in the apparatus a separate mechanical switch to shut off the magnetron or system when air flow is halted or slowed to an objectionable extent. Such a switch is shown at 107. When after start-up, air flow ceases, the vane 109 drops to vertical position and the switch opens, cutting off power to the magnetron or the whole system (or selected parts thereof). When sufficient air flow is present, showing that the blower is operating properly, the magnetron continues to generate microwave radiation because the air flow deflects the vane.

The arrows in FIG. 5 show the two different paths of solvent vapor to the detector 101. Arrows 115, 117, 119 and 121 represent the path of the solvent vapor from the extraction container to the collection container and thence to the exhaust ductwork. Arrows 123 and 125 show how any solvent vapor that might have leaked into the microwave chamber is exhausted to ductwork 105 through blower or fan 103. Arrow 127 shows how the solvent vapor is directed to the detector and arrows 129 and 131 represent discharge of the solvent vapor to an exhaust outside the building or to recovery and/or treatment stations. In FIG. 5 and in FIGS. 2 and 4 there is shown tube 35, through which any solvent vapor that is vented to the collection container 33 is transported to detector 101 (FIG. 5). While that is a preferred embodiment of the present invention it is within the invention to utilize air passing through the microwave chamber to pick up any solvent vapor that might have been released by the extraction vessel 27, the collection container 33 or the connecting tubing 31 and 35 by having passed into contact with or near said components of the present system or other components of it.

Another feature of the invented apparatus illustrated in FIG. 5 is the sheet 111 of Teflon or other suitable insulating polymer, preferably a fluoropolymer, e.g., PTFE or PFA, that covers the ceiling 15 of the microwave chamber. Such sheet is held to the ceiling by polypropylene dart clips 113 or other suitable insulating fasteners. As is indicated, it covers lamp 23 too. Thus, it prevents sparking between the chamber ceiling and other parts of the apparatus and prevents an overheated lamp from igniting solvent vapors, if such are present in the microwave chamber near the ceiling.

Figure 6:
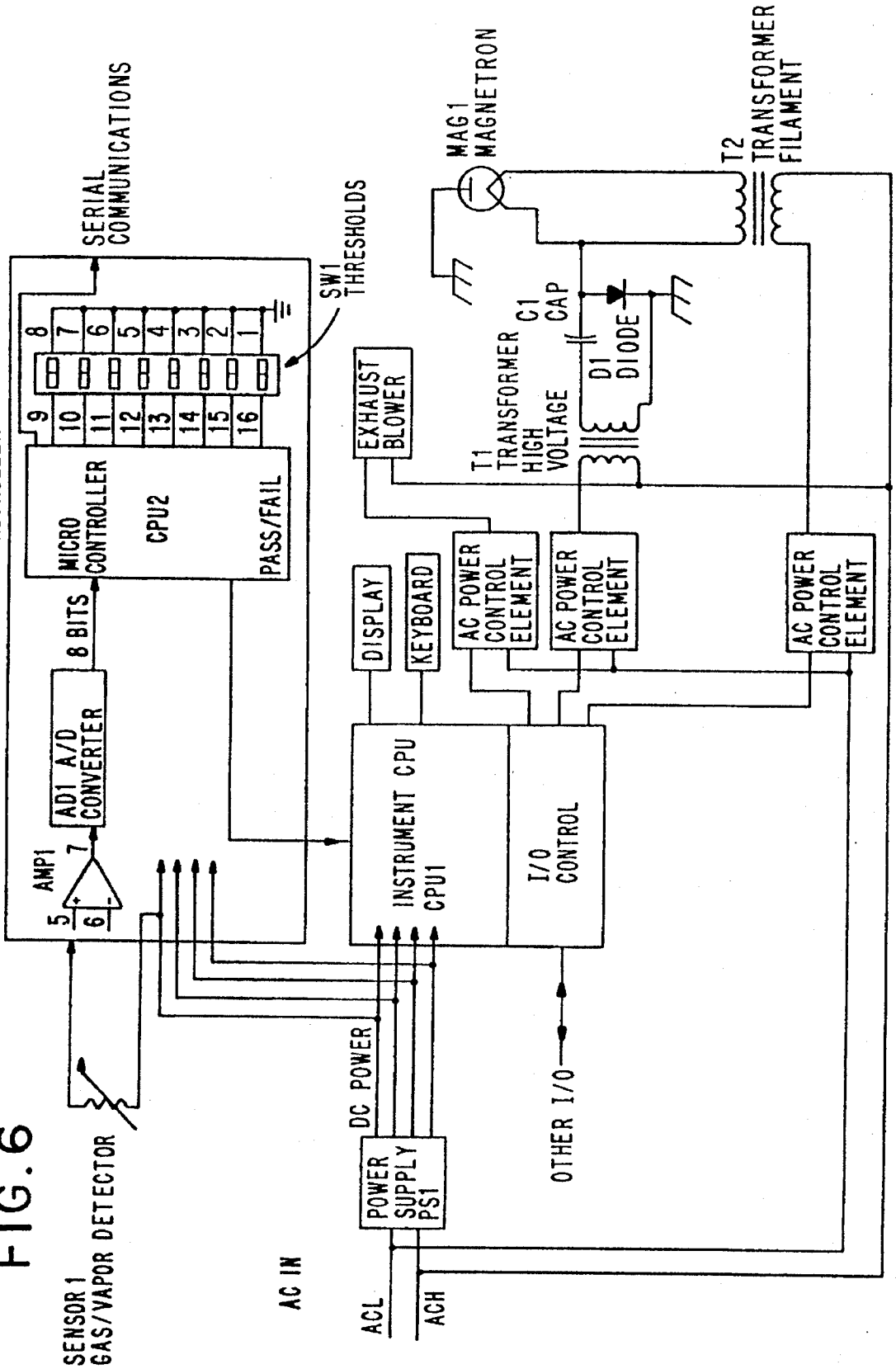
FIG. 6 is an electrical wiring diagram for the invented apparatus.

FIG. 6 is self-explanatory and therefore will not be discussed at length herein. Suffice it to say that it shows the circuitry utilized to power the solvent vapor detector and the magnetron and shows how the detector controls operation of the magnetron, turning it off when solvent vapor is detected. In a similar manner the circuitry may be modified so that all the system (except the detector, if desired) or part thereof may be deenergized if solvent vapor is detected. Preferably, the magnetron is not automatically turned back on when the solvent vapor is no longer present, but manual switching is required to reactivate the system.

The various parts of the apparatus are known in the art and may be readily obtained commercially. The basic microwave system, including a magnetron, which is the source of microwave radiation, a chamber, in which the material to be heated is placed, a turntable, which keeps the material in motion so that it is evenly exposed to the microwave radiation, an exhaust fan, to keep air circulating through the chamber, a collection container, to collect any material discharged from an extraction container if the rupture diaphragm in it is ruptured, computer control circuitry connections to a source of electrical power, a control panel 16 (FIG. 1) and a readout panel, may be those of CEM Corporation's MDS-81-D microwave digestion apparatus or other equivalent microwave system. Such a system, except for the collection container, is described in U.S. Pat. No. 3,909,598, issued to CEM Corporation, and can operate at any of various power levels, up to 2000 watts.

The extraction container is described in European patent 0,416,759 but any of many other suitable microwave transmissive containers may also be employed. Such containers are usually of polymeric plastic material, are heat resistant and pressure resistant, and are not adversely affected by the solvent being employed. The most preferred containers are those which are fiberglass reinforced polyetherimide (Ultem) lined with fluoropolymer (Teflon PFA). The collection container and the various fittings for connecting the containers to other parts of the system are preferably of fluoropolymer too, as are the tubes and ducts that carry any solvent vapor but the vapor carrying parts may be of other materials too because they rarely will be subjected to contact with solvent (and then only with vapor). The tubing connecting the collection container with extraction containers is preferably Teflon tubing which is about 3 mm inside diameter but tubing i.d's. in the range of 2 to 5 mm are also suitable, as are i.d's. outside that range. The tubing connecting the collection container and the detector will preferably be about 6 mm. i.d. but may be in the range of 3 mm to 1 cm i.d. and beyond, as befits the situation.

The extraction solvent employed will be sufficiently polar so as to convert the microwave radiation to heat and to be heated by it, which promotes extraction. Non-polar solvents, such as hexane and petroleum ether, may be used but will normally have present with them a polar solvent, such as a ketone, an alcohol or water, either in the solvent medium or in the material to be extracted, so as to promote conversion of the radiation to heat. The temperature to which the solvent may be heated will depend on the equipment design, the material being extracted and the solvent. Temperatures within the range of 40° to 200° C., e.g., 100° to 200° C., can be employed and pressures in the extraction vessel may be as high as 1,000 lbs./sq. in., although it is preferred to limit them to about 500 or 600 lbs./sq. in. and often to about 200 lbs./sq. in.

The detector, which detects the presence of solvent vapor in gas passing by it, is preferably of the semiconductor gas sensor type and the semiconductor is preferably tin dioxide. It is preferably specifically designed for detecting the presence of organic solvent vapors in a gas stream passing over it and its resistance decreases in the presence of such vapor. Such conductivity increase increases voltage output from the sensor and that increase actuates a relay, switch or appropriate circuitry, turning off the magnetron or electrical system when the presence of solvent vapor is detected. The preferred gas sensor is that manufactured by Figaro Engineering Inc. and sold by them as their Figaro Gas Sensor TGS822, the details of which are described in their 8 page leaflet of that title, which was published in 1989 and which is hereby incorporated herein by reference. However, other sensors may also be employed, including infrared sensors, which measure transmission of infrared radiation through the gas being sensed, utilizing a photovoltaic cell, and other similar radiation transmission detectors which are solvent vapor sensitive.

The electric circuitry by which the magnetron or the system is controlled in response to the detection of solvent vapor in the exhaust from the chamber (or from the collection container) may be varied in any manner, known to those of skill in electronics, to accomplish the desired safe operation of the system and to prevent the accumulation of any potentially dangerous solvent vapor/air mixtures in the microwave chamber. Instead of turning off the magnetron when any solvent vapor is detected the entire system (or parts of it) may be shut down and the circuitry may be designed so as to prevent resumption of magnetron or system functions until manually activated.

The vane-type switch illustrated in the exhaust duct elbow may be of any microswitch type or may be of a relay type. Alternatively, it may be a miniature fan-type generator which can turn circuitry on or off, depending on air flow. Also, another gas sensor of the semiconductor type, chosen for its increased sensitivity to air flow rate, can be utilized as a backup for the main solvent sensitive semiconductor type sensor. The sensor circuitry may be set to activate the magnetron control switch when the fan is shut off completely (which is usually due to operator error or fan or blower failure) or when the air flow has been reduced to less than design flow (such as to less than 70 to 80% of such flow rate). In either case the conductivity of the detector (or the microswitch operation) will be such that the magnetron or other source of microwave radiation, or the system or part of it, will be shut down for safety's sake.

The ceiling cover that protects the microwave chamber against sparking and against high lamp tempertues is preferably a sheet of fluoropolymer, such as Teflon PFA or PTFE, but other insulating polymers that are resistant to solvents employed may also be used, including polyethylene and polypropylene. Preferably the cover will be in flat sheet form of a thickness in the range of about 1 to 4 mm, such as about 2.5 mm. It will be held by appropriate non-conductive fasteners to the chamber ceiling, preferably being held by dart clips that fit holes in such ceiling, which clips are preferably of polypropylene, but can be of any suitable non-conductive plastic or similar material. When employed to cover a light and to lower the temperature at the ceiling by it, as well as to prevent arcing from a metal mode stirrer (the location of which is not specifically indicated in the drawing) if it touches the ceiling, the plastic cover should be large enough to cover the light and to prevent such contact of the mode stirrer with the ceiling but it does not have to cover the entire ceiling, although that is preferred.

The following examples illustrate processes of the invention in which an apparatus thereof is employed. Unless otherwise indicated all parts given in the examples and in this specification are by weight and all temperatures are in °C.

EXAMPLE 1

To simulate operation of the explosion proof apparatus a known quantity of n-hexane (solvent) vapor is injected into the microwave chamber of the apparatus illustrated in FIGS. 1–6 and is detected by the Figaro TGS822 gas sensor, which turns off the magnetron, thereby protecting the apparatus against a chamber explosion. 50 Ml of n-hexane vapor, at atmospheric pressure and also at room temperature are injected into a microwave chamber which is of a volume of 42.5 liters (1.5 cubic feet), which equates to a concentration of the n-hexane in air that is ¹⁄₁₀ of the lowest explosive limit (which LEL is 1.2% by volume) and the gas mixture is then delivered to the detector by the illustrated blower (103 of FIG. 5), which propels such mixture at a rate of 119 cubic feet per minute, and thereby further dilutes the mixture to some extent. Still, even at such a low concentration of the solvent vapor in air the detector turns off the magnetron (or can be wired to turn off the whole system or parts of it). Such result is especially notable because the voltage difference generated due to the presence of n-hexane vapor at the detector is less than that for many other solvent vapors and solvent vapor mixtures from the solvents and mixtures normally employed as extractants in microwave extractions. Similar results are obtainable when the n-hexane vapor is in the collection container, due to rupture diaphragm "failure" and is drawn into the exhaust duct and past the detector. Also, when the fan or blower is slowed to 0%, 50% and 70% of the design rate the detector turns off the magnetron. When the Figaro detector is disconnected and only the vane switch is utilized the magnetron is turned off when the air flow is shut off or is diminished to 70% of the design rate (or 83 cubic feet per minute), or less.

EXAMPLE 2

When the experiment of Example 1 is repeated, but with the injection of other solvent vapors into the chamber 13 instead of n-hexane, through blower 103 to detector 101 or from container 27 through collection container 33 and through tubes 35 and 99 to outlet 100 and detector 101 (FIG. 5) the magnetron is also shut down. The solvents employed, all of which are used to extract toxic wastes, treated toxic wastes, dried sewage sludge, food products and additives, plastics, drugs, cosmetics, soils and plant parts, include cyclohexane, petroleum ether, acetone, methanol, ethanol, 2-propanol, 1:1 (by volume) n-hexane acetone mixture, 1:1 (by volume) petroleum ether:acetone mixture, and any mixtures thereof in various proportions, and may also include water. In such extractions the extracting solvent will be microwave heated to a temperature in the 100° to 200° range, at which the pressure will be in the range of 50 to 300 lbs./sq. in. gauge. Whereas in the circuitry illustrated in FIG. 6 the increase in voltage due to the presence of the 50 ml of n-hexane vapor in the apparatus chamber is only 0.3 volt, to which the circuitry is sufficiently sensitive to shut down the magnetron, for 50 ml of petroleum ether vapor it is 0.55 volt, for 50 ml of methanol vapor it is 3.8 volts, for 50 ml of 2-propanol vapor it is 1.7 volts, and for 5 ml of acetone it is 0.64 volt. Also, for the 1:1 (by volume) n-hexane:acetone vapor mixture the voltage increase is 1.9 volts when 25 ml are injected and for the 1:1 (by volume) petroleum ether: acetone vapor mixture the voltage increase is 1.8 volts when 25 ml are injected, each of which increases is greater than would have been expected from the components of the vapors. Thus, the presences of such solvent vapors or vapor mixtures in the microwave chamber or in the exhaust from the collection container results in turnings off of the magnetron (or the system), which prevents any explosion in the chamber. Also, the presence of the Teflon shield over the ceiling light lowers the temperature at that location and the shield also prevents any arcing between a metal mode stirrer and a metal ceiling, which otherwise could cause an explosion if there was present an explosive combination of solvent vapor and air at that location.

EXAMPLE 3

The invention described in Examples 1 and 2 is adaptable to other operations which also involve microwave heatings of solvents, such as preparations of reagents wherein heated solvents are utilized, evaporations, distillations, digestions and chemical reactions, including syntheses, analyses and hydrolyses. In short, it is applicable to any operations in which an explosive atmosphere can be created by escape of a potentially explosive solvent vapor or other potentially explosive vapor into a microwave chamber or microwave system part from an otherwise closed system. Among such operations are those wherein air passing through the microwave chamber in contact with or near the extracting container or the collection container or the connecting tubing picks up any solvent vapor leaking from any of those and delivers it to the detection device(s), with or without the presence of the collection container or connecting tubing in the system. Also, various other solvents and combinations of solvents than those described previously may be employed so long as the polarity thereof is sufficient to absorb microwave radiation and heat the extracting solvent and the material being extracted by it. However, mixtures of the hydrocarbon:ketone type are usually preferable.

The invention has been described with respect to various illustrations and working embodiments thereof but it is not to be considered as being limited to them because one of skill in the art, with the present description before him or her, will be able to utilize substitutes and equivalents without departing from the invention.

What is claimed is:

1. An explosion proof microwave heated solvent extraction apparatus for extracting materials with an organic extracting solvent which is explosive in air, which apparatus comprises a walled chamber, a source of microwave radiation into said chamber, a microwave transmissive extraction container in said chamber, adapted to contain, under pressure, said organic extracting solvent, base material and extractable material with the base material, which extractable material is extractable by the solvent while the solvent is being heated by the microwave radiation, means for passing air through the chamber in an inlet and out an outlet in the chamber, means for detecting the presence of the solvent in said air leaving the chamber, and for modifying an electrical signal in response to the presence of the solvent in said air, said means comprising a switch that requires manual operation to reactivate the source of microwave radiation, and means for controlling operation of the source of microwave radiation in response to said modified electrical signal so that radiation from said source is terminated when the solvent is detected in the air leaving the chamber at a concentration which is not more than a predetermined explosive concentration.

2. An apparatus according to claim 1 wherein safety rupture means, a collection container and connecting tubing are associated with the container, which rupture means ruptures when pressure in the container exceeds a predetermined safe limit, and thereby releases contents, including solvent vapor, from the extraction container through connecting tubing into the collection container from which the solvent vapor is drawn into the air passing through the chamber.

3. An apparatus according to claim 2 wherein gas exhausting means is provided to remove gases from the walled chamber through the outlet, the means for detecting the presence of solvent in the air leaving the chamber is a solvent vapor detector which is located so as to be in the path of the air leaving the chamber, and the gas exhausting means acts to exhaust gas from the collection container and into contact with the solvent vapor detector.

4. An apparatus according to claim 3 wherein the gas exhausting means is a blower or fan which exhausts gas from the chamber to outside the apparatus or to a collection or treatment system through a passageway, the solvent vapor detector is located in said passageway outside the microwave chamber, and the collection container is connected to said passageway upstream of the solvent vapor detector.

5. An apparatus according to claim 4 wherein the collection container is connected to the passageway by tubing adapted to convey gas from the collection container to the detector and said tubing terminates in an angled opening in the passageway so as to create a venturi type effect and draw gas from the collection container to the detector when the blower or fan is in operation.

6. An apparatus according to claim 5 which comprises a relay, switch or electrical circuitry to control the source of microwave radiation, and wherein the solvent vapor detector is a semiconductor gas sensor which is capable of detecting organic solvent vapors by decreasing its electrical resistance in the presence of such organic solvent vapor, which decrease in resistance increases voltage at the detector and operates the relay, switch or electrical circuitry, which in turn turns off the source of microwave radiation when the presence of organic solvent vapor is detected by the detector.

7. An apparatus according to claim 6 wherein the semiconductor gas sensor is of the tin dioxide type and is also sensitive to air flow so that voltage at the detector is increased when air flow is slowed or is halted, which causes the source of microwave radiation to be turned off when solvent vapor is detected or when air flow is halted.

8. An apparatus according to claim 6 which comprises a separate air flow detector which acts to turn off the source of microwave radiation when air flow is halted.

9. An apparatus according to claim 8 wherein the separate air flow detector is a mechanical air flow detector which is moved in response to air flow so as to hold a switch or relay in closed position in which electricity is supplied to a magnetron, which is the source of microwave radiation into the chamber, and is moved to open switch position when said air flow ceases, to turn off the magnetron.

10. A microwave heated solvent extraction apparatus for extracting materials with an organic extracting solvent, the vapor of which is explosive in air, which apparatus comprises a walled chamber, a source of microwave radiation into said chamber, a microwave transmissive extraction container in said chamber, adapted to contain, under elevated temperature and pressure, said extracting solvent, base material and extractable material with the base material, an inlet to the chamber and an outlet from the chamber, through which inlet, chamber and outlet air can be passed, means for passing air through said inlet, chamber and outlet past the container so that any said solvent vapor escaping from said container will be carried through the outlet with the air, means for detecting presence of said solvent vapor in said air after they pass through the outlet and for modifying an electrical signal in response to the presence of said solvent vapor in said air, means for controlling operation of the source of microwave radiation in response to said modified electrical signal from said detecting means, means for delivering said modified electrical signal from said detecting means to said controlling means, means for detecting absence of air flow in the apparatus downstream of the chamber and means for shutting down the source of microwave radiation when said absence of air flow is detected by said flow detecting means.

11. An apparatus according to claim 10 wherein the means for detecting absence of air flow downstream of the chamber is separated from the means for detecting presence of solvent vapor.

12. An apparatus according to claim 10 wherein the means for detecting presence of solvent vapor is also sensitive to air flow so that when air flow is halted it causes the source of microwave radiation to be turned off.

13. An apparatus according to claim 10 which comprises a rupture means on the extraction container which ruptures at a predetermined safe pressure limit, a collection container for collecting any material ejected from the extraction container upon rupture of the rupture means, means for connecting the extraction container with the collection container so that material ejected from the extracting container is passed to the collection container, and means for passing any solvent vapor in an upper portion of the collection container to the air exiting the chamber, at a location before the means for detecting the presence of solvent vapor in said air.

14. A microwave heated solvent extraction apparatus for extracting materials with an organic extracting solvent, the vapor of which is explosive in air, which apparatus comprises a walled chamber, a source of microwave radiation into said chamber, a microwave transmissive extraction container in said chamber, adapted to contain, under elevated temperature and pressure, said extracting material, base material and extractable material with the base material, which extractable material is extractable by said solvent while said solvent is being heated by said microwave radiation, means for passing air through said chamber in an inlet to and out an outlet from said chamber, means for detecting presence of said solvent in said air leaving said chamber and for modifying an electrical signal in response to said detecting of said solvent in said air, means for controlling operation of said source of microwave radiation in response to said modified electrical signal so that when said solvent is detected by said detector microwave radiation from the source thereof is terminated, and an air flow detector which comprises means for turning off said source of microwave radiation when said air flow ceases, whereby said apparatus is protected against possible explosions when solvent escapes from said extraction container during microwave heating of the contents thereof.

15. An extraction apparatus according to claim 14 wherein said means for detecting the presence of solvent is a semiconductor gas sensor which is sensitive to air flow so that it terminates said microwave radiation when solvent vapor is detected, when air flow ceases, and when both such conditions exist.

16. An extraction apparatus according to claim 14 wherein said means for detecting the presence of solvent is a semiconductor gas sensor and said air flow detector is a mechanical detector which is moved in response to air flow so as to hold a switch or relay in closed position, in which electricity is supplied to said source of microwave radiation, and is moved to open position when said air flow ceases, to turn off said source of microwave radiation.

17. An explosion proof microwave heated solvent extraction apparatus which comprises a source of microwave radiation, a walled chamber into which such microwave radiation is directed, which chamber includes an inlet through which air can enter the chamber and an outlet through which air can exit the chamber, a microwave transmissive extraction container in said chamber, adapted to contain, under pressure, extracting solvent medium and material to be extracted, safety rupture means associated with the extraction container, which rupture means ruptures when the pressure in the container is at a predetermined safe limit and thereby releases solvent vapor from the extraction container, a collection container into which the released solvent vapor and any entrained solvent liquid are directed and in which they are collected, means for passing air into the chamber through the inlet and out of the chamber through the outlet, and a solvent vapor detector constructed and positioned for detecting the presence of solvent vapor from the collection container, which solvent vapor detector controls operation of the source of microwave radiation so as to shut down said source when solvent vapor is detected by said detector at a concentration which is not more than a predetermined explosive concentration.

\* \* \* \* \*